(12) United States Patent
Heller

(10) Patent No.: US 7,865,974 B1
(45) Date of Patent: Jan. 11, 2011

(54) EAR COVERING METHOD

(76) Inventor: Melissa E. Heller, 403 N. Palm Dr., Apt. #1, Beverly Hills, CA (US) 90210

( * ) Notice: Subject to any disclaimer, the term of this patent is extended or adjusted under 35 U.S.C. 154(b) by 53 days.

(21) Appl. No.: 12/033,679

(22) Filed: Feb. 19, 2008

(51) Int. Cl.
*A42B 1/06* (2006.01)
(52) U.S. Cl. .......................................................... 2/209
(58) Field of Classification Search ............. 2/209, 2/174, 208, 423, 455; 132/319, 212, 213, 132/270
See application file for complete search history.

(56) References Cited

U.S. PATENT DOCUMENTS

| 2,570,675 | A | | 10/1951 | Heflin | |
| 4,660,229 | A | | 4/1987 | Harris | |
| D331,130 | S | | 11/1992 | Williams | |
| 5,689,831 | A | * | 11/1997 | Harris | 2/209 |
| 5,778,455 | A | | 7/1998 | Joseph | |
| 6,298,493 | B1 | | 10/2001 | Ambroise | |
| 6,944,886 | B1 | * | 9/2005 | Jackson | 2/209 |
| 7,614,089 | B2 | * | 11/2009 | Hillman-Schwartz et al. | 2/174 |
| 2001/0029622 | A1 | | 10/2001 | Bose et al. | |

* cited by examiner

*Primary Examiner*—Tejash Patel

(57) ABSTRACT

An ear covering method includes providing a covering comprised of a flexible and water impermeable material. The covering has an outer wall, an inner wall and a perimeter wall extending between the outer and inner walls. The inner wall has an aperture extending therethrough to access an interior of the covering. An adhesive is mounted on an outer surface of the inner wall. A person's ear is extended through the aperture and the adhesive secures the inner wall to skin adjacent to the ear.

14 Claims, 3 Drawing Sheets

US 7,865,974 B1

EAR COVERING METHOD

BACKGROUND OF THE INVENTION

Field of the Invention

The present invention relates to ear covering devices and more particularly pertains to a new ear covering device for preventing water and soap from entering and irritating an ear canal while a person bathes.

SUMMARY OF THE INVENTION

The present invention meets the needs presented above by generally comprising a covering comprised of a flexible and water impermeable material. The covering has an outer wall, an inner wall and a perimeter wall extending between the outer and inner walls. The inner wall has an aperture extending therethrough to access an interior of the covering. An adhesive is mounted on an outer surface of the inner wall. A person's ear is extended through the aperture and the adhesive secures the inner wall to skin adjacent to the ear.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
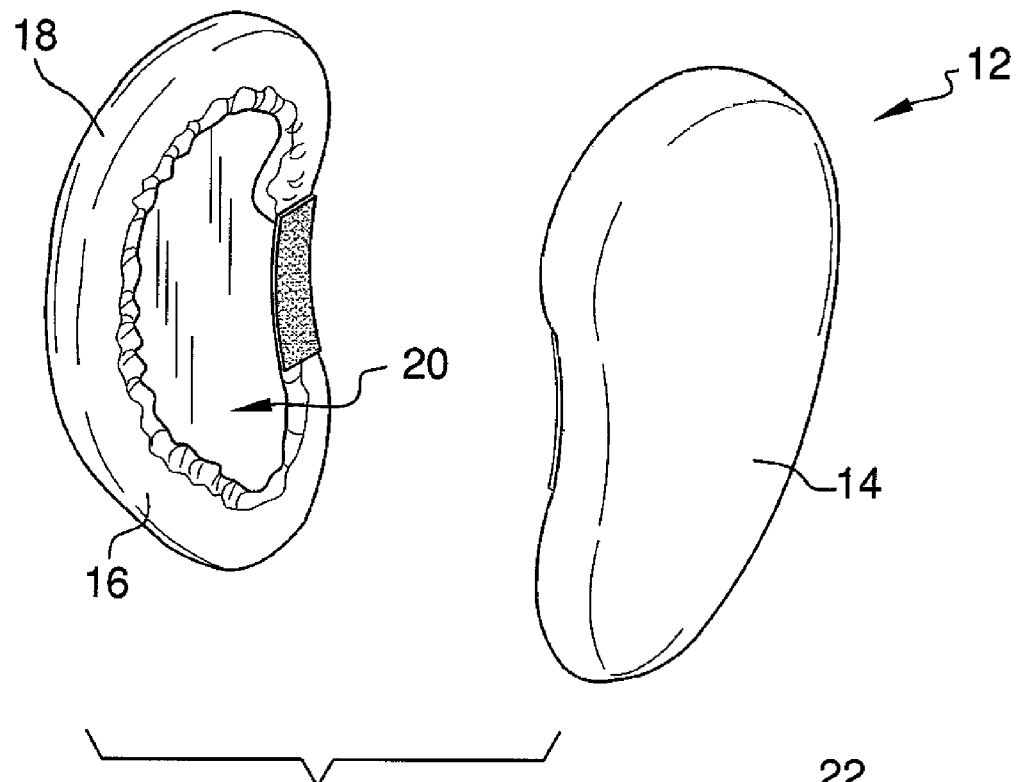
FIG. 1 is a perspective view of a pair of ear coverings of a method according to the present invention.
Figure 2:
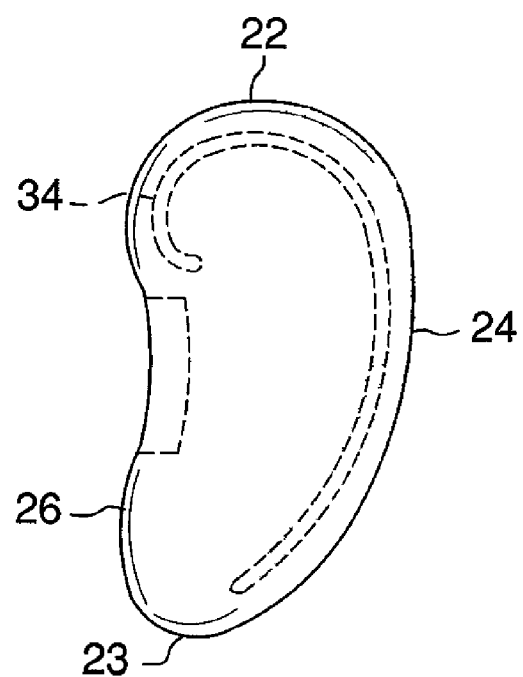
FIG. 2 is a left side view of the present invention.
Figure 3:
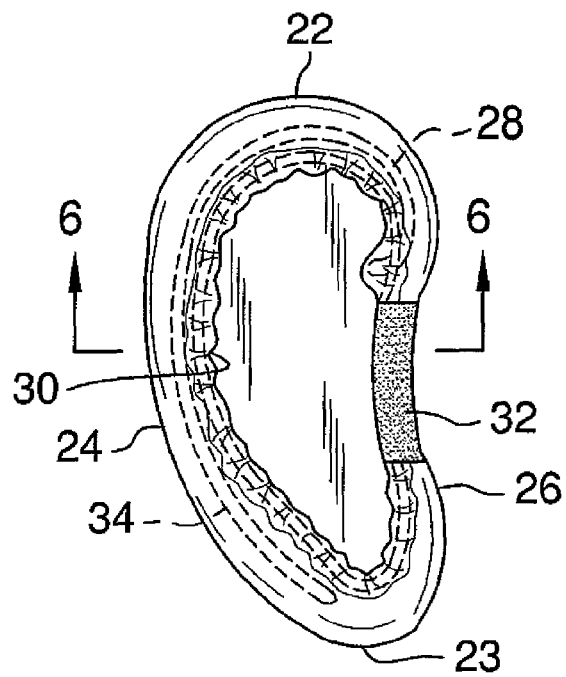
FIG. 3 is a right view of the present invention.
Figure 4:
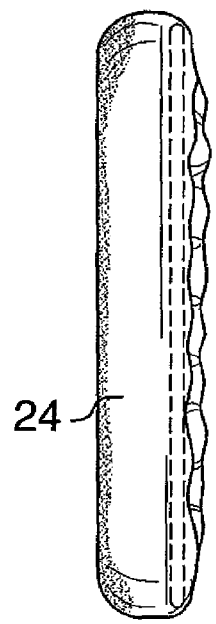
FIG. 4 is a rear view of the present invention.
Figure 6:
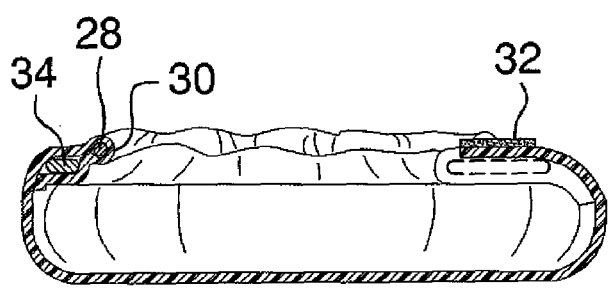
FIG. 6 is a cross-sectional view taken along line 6-6 of FIG. 3 of the present invention.
Figure 5:
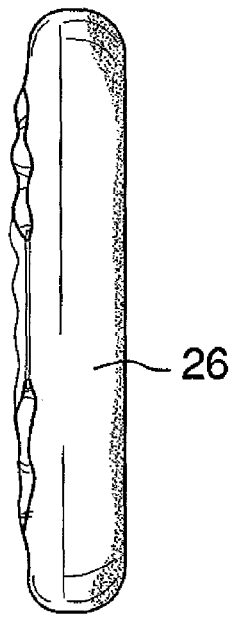
FIG. 5 is a front view of the present invention.
Figure 7:
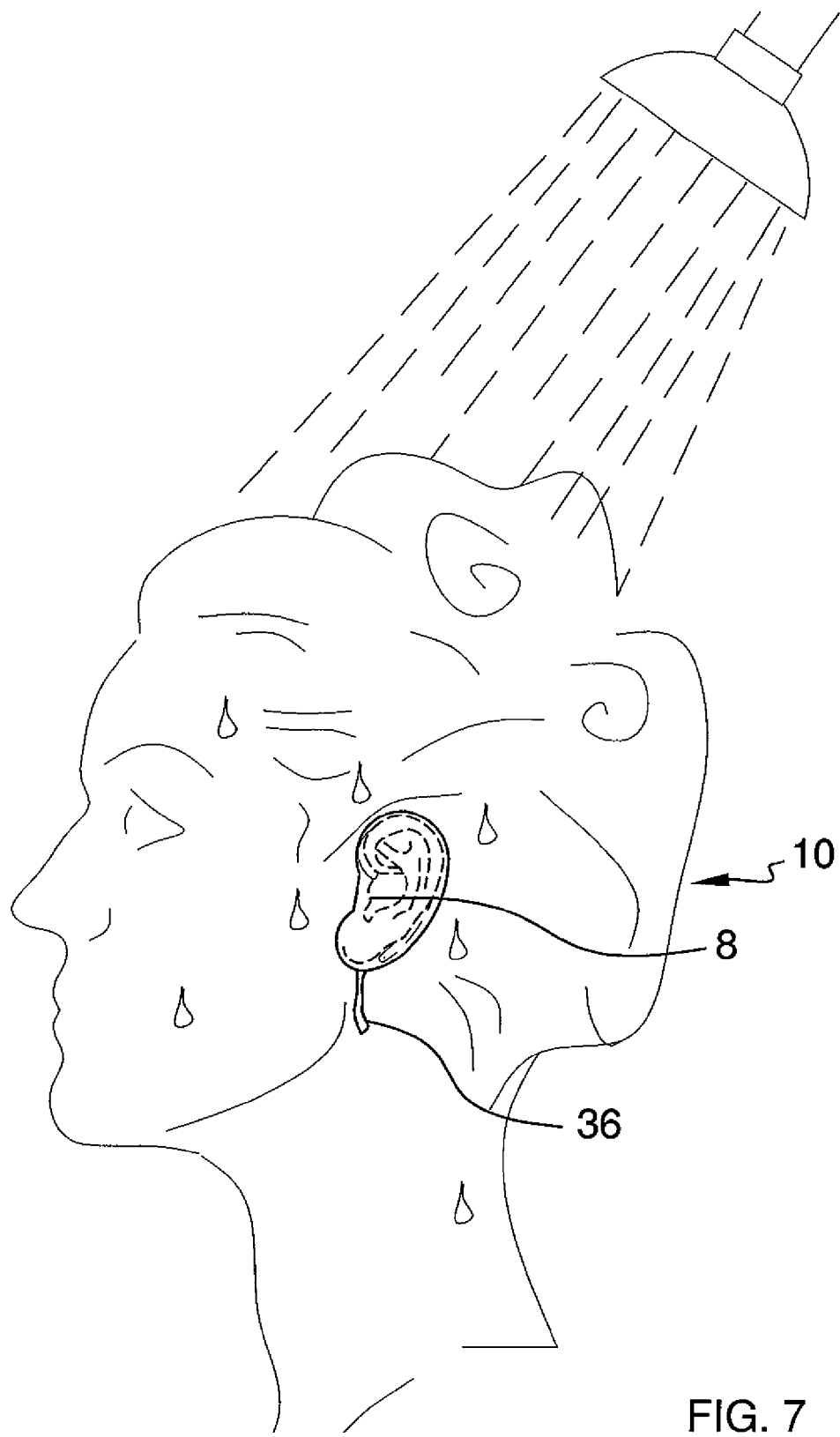
FIG. 7 is a side in-use view of the present invention.

With reference now to the drawings, and in particular to FIGS. 1 through 7 thereof, a new ear covering device embodying the principles and concepts of the present invention and generally designated by the reference numeral 10 will be described.

As best illustrated in FIGS. 1 through 7, the ear covering method 10 generally providing a covering 12 comprised of a flexible and water impermeable material. The covering 12 has an outer wall 14, an inner wall 16 and a perimeter wall 18 extending between the outer 14 and inner 16 walls. The inner wall 16 has an aperture 20 extending therethrough to access an interior of the covering 12. The perimeter wall 18 includes a top wall 22, a bottom wall 23, a first lateral wall 24 and a second lateral wall 26. Each of the top 22, bottom 23 and first lateral 24 walls is convexly arcuate. The second lateral wall 26 is concavely arcuate. The covering 12 has a height dimension from the top wall 22 to the bottom wall 23 of the perimeter and width dimension from the first lateral wall 24 to the second lateral wall 26. The height dimension is less than 3.5 inches and the width dimension is less than 2.5 inches.

A band 28 is attached to and extends along an edge 30 of the aperture 20. The band extends along the entire portion of the aperture but for an area adjacent to the second lateral wall 26. The band 28 is resiliently stretchable and may be comprised of an elastomeric material. The band 28 draws the aperture 20 closed such as when the edge 30 of the aperture 20 is extended around an ear 8. The band 28 may also be coextensive with the edge 30.

An adhesive 32 is mounted on an outer surface of the inner wall 16. The adhesive 32 may comprise any conventional pressure sensitive adhesive. A removable covering, not shown, may be positioned on the adhesive 32 until it is ready to be used. The adhesive 32 is adhered to skin 32 of the user to help retain the covering on the ear 8.

A framing member 34 is positioned within the covering 12. The framing member 34 is positioned within the inner wall 16 and is extends along the top 22 and first lateral 24 walls. The framing member 34 is comprised of a resiliently flexible material. The framing member 34 assists either or both of the adhesive 32 and band 28 in retaining the cover 12 on the ear 8.

In use, the user of the covering 12 extends their ear 8 through the aperture 20 and secures the inner wall 16 to skin adjacent to the ear 8. The user then bathes and may clean their hair without water and soap entering the ear canal. A tether 36 may be attached to the covering 12 to assist the person in removing or placing the covering 12 on the ear 8.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of preventing water entering a person's ear while bathing, said method comprising the steps of:

providing a covering comprised of a flexible and water impermeable material, said covering having an outer wall, an inner wall and a perimeter wall extending between said outer and inner walls, said inner wall having an aperture extending therethrough to access an interior of said covering, said perimeter wall including a top wall, a bottom wall, a first lateral wall and a second lateral wall, each of said top, bottom and first lateral walls being convexly arcuate, said second lateral wall being concavely arcuate, said covering having a height dimension from said top wall to said bottom wall of said perimeter and width dimension from said first lateral wall to said second lateral wall, said height dimension being less than 3.5 inches, said width dimension being less than 2.5 inches;

providing a band being attached to and extending along an edge of said aperture, said band being resiliently stretchable;

providing an adhesive being mounted on an outer surface of said inner wall;

providing a framing member being positioned within said covering, said framing member being positioned within said inner wall and being extending along said top and first lateral walls, said framing member being comprised of a resiliently flexible material;

providing a tether being attached to said covering for assisting the person in placing said covering on the ear; and extending the ear through said aperture and securing said inner wall to skin adjacent to said ear with said adhesive.

2. A method of preventing water entering a person's ear while bathing, said method comprising the steps of:

providing a covering comprised of a flexible and water impermeable material, said covering having an outer wall, an inner wall and a perimeter wall extending between said outer and inner walls, said inner wall having an aperture extending therethrough to access an interior of said covering, said perimeter wall having a top wall, a bottom wall, a first lateral wall and a second lateral wall, each of said top, bottom and first lateral walls being convexly arcuate, said second lateral wall being concavely arcuate;

providing an adhesive being mounted on an outer surface of said inner wall;

providing a tether being attached to said covering for assisting the person in placing said covering on the ear; and extending the ear through said aperture and securing said inner wall to skin adjacent to said ear with said adhesive.

3. The method according to claim 2, wherein the step of providing said covering further includes said covering having a height dimension from said top wall to said bottom wall of said perimeter and width dimension from said first lateral wall to said second lateral wall, said height dimension being less than 3.5 inches, said width dimension being less than 2.5 inches.

4. The method according to claim 2, further including the step of providing a band being attached to and extending along an edge of said aperture, said band being resiliently stretchable.

5. The method according to claim 4, further including the step of providing a framing member being positioned within said covering, said framing member being positioned within said inner wall and being extending along said top and first lateral walls.

6. The method according to claim 5, wherein the step of providing said framing member further includes said framing member being comprised of a resiliently flexible material.

7. The method according to claim 2, further including the step of providing a framing member being positioned within said covering, said framing member being positioned within said inner wall and being extending along said top and first lateral walls.

8. The method according to claim 7, wherein the step of providing said framing member further includes said framing member being comprised of a resiliently flexible material.

9. A method of preventing water entering a person's ear while bathing, said method comprising the steps of:

providing a covering comprised of a flexible and water impermeable material, said covering having an outer wall, an inner wall and a perimeter wall extending between said outer and inner walls, said inner wall having an aperture extending therethrough to access an interior of said covering;

providing an adhesive being mounted on an outer surface of said inner wall;

providing a tether being attached to said covering for assisting the person in placing said covering on the ear;

providing a framing member being positioned within said covering, said framing member being positioned within said inner wall and being extending along said top and first lateral walls; and extending the ear through said aperture and securing said inner wall to skin adjacent to said ear with said adhesive.

10. The method according to claim 9, wherein the step of providing said covering further includes said perimeter wall having a top wall, a bottom wall, a first lateral wall and a second lateral wall, each of said top, bottom and first lateral walls being convexly arcuate, said second lateral wall being concavely arcuate, wherein the step of providing said covering further includes said covering having a height dimension from said top wall to said bottom wall of said perimeter and width dimension from said first lateral wall to said second lateral wall, said height dimension being less than 3.5 inches, said width dimension being less than 2.5 inches.

11. The method according to claim 9, further including the step of providing a band being attached to and extending along an edge of said aperture, said band being resiliently stretchable.

12. The method according to claim 11, further including the step of providing a framing member being positioned within said covering, said framing member being positioned within said inner wall and being extending along said top and first lateral walls.

13. The method according to claim 12, wherein the step of providing said framing member further includes said framing member being comprised of a resiliently flexible material.

14. The method according to claim 9, wherein the step of providing said framing member further includes said framing member being comprised of a resiliently flexible material.

* * * * *